United States Patent
Xie et al.

(10) Patent No.: US 10,695,715 B2
(45) Date of Patent: Jun. 30, 2020

(54) CARBONIZED MATERIAL, DEVICE FOR REMOVING OZONE, AND METHOD FOR REMOVING OZONE

(71) Applicant: Industrial Technology Research Institute, Hsinchu (TW)

(72) Inventors: Wen-An Xie, New Taipei (TW); Hong-Ping Lin, Taipei (TW); Shou-Nan Li, Caotun Township (TW); Hui-Ya Shih, Puyan Shiang (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 127 days.

(21) Appl. No.: 15/814,823

(22) Filed: Nov. 16, 2017

(65) Prior Publication Data

US 2018/0369751 A1 Dec. 27, 2018

(30) Foreign Application Priority Data

Jun. 22, 2017 (TW) .............................. 106120874 A

(51) Int. Cl.

| | | |
|---|---|---|
| *C01B 31/00* | (2006.01) | |
| *B01D 53/66* | (2006.01) | |
| *C07B 63/02* | (2006.01) | |
| *C01B 13/02* | (2006.01) | |
| *C07G 99/00* | (2009.01) | |
| *B01J 20/30* | (2006.01) | |
| *B01J 20/20* | (2006.01) | |
| *C01B 32/00* | (2017.01) | |
| *C01B 32/50* | (2017.01) | |
| *C07C 69/00* | (2006.01) | |
| *C07C 53/00* | (2006.01) | |
| *C07C 47/02* | (2006.01) | |
| *C07B 33/00* | (2006.01) | |

(52) U.S. Cl.

CPC .............. *B01D 53/66* (2013.01); *B01J 20/20* (2013.01); *B01J 20/3078* (2013.01); *C01B 13/0203* (2013.01); *C01B 32/00* (2017.08); *C07B 63/02* (2013.01); *C07G 17/00* (2013.01); *B01D 2251/104* (2013.01); *B01D 2251/21* (2013.01); *B01D 2251/70* (2013.01); *B01D 2253/102* (2013.01); *B01J 2220/485* (2013.01); *C01B 32/50* (2017.08); *C01B 2210/0006* (2013.01); *C01B 2210/0092* (2013.01); *C07B 33/00* (2013.01); *C07C 47/02* (2013.01); *C07C 53/00* (2013.01); *C07C 69/00* (2013.01)

(58) Field of Classification Search

CPC ................................................... C01B 32/00

See application file for complete search history.

(56) References Cited

U.S. PATENT DOCUMENTS

| | | | |
|---|---|---|---|
| 3,090,731 A | 5/1963 | Keil | |
| 3,516,783 A | 6/1970 | Blanchard | |
| 4,259,299 A | 3/1981 | Hagiwara et al. | |
| 4,552,863 A | 11/1985 | Fujimori | |
| 4,831,011 A * | 5/1989 | Oikawa ................... | B01J 20/20 422/5 |
| 6,902,589 B1 | 6/2005 | Guderian et al. | |
| 9,234,148 B2 | 1/2016 | Ullrich | |

FOREIGN PATENT DOCUMENTS

| | | |
|---|---|---|
| CN | 101357331 A | 2/2009 |
| CN | 102247757 A | 11/2011 |
| CN | 102311742 A | 1/2012 |
| CN | 103084184 A | 5/2013 |
| CN | 104001502 A | 8/2014 |
| CN | 105312061 A | 2/2016 |
| JP | 2-144146 A | 6/1990 |
| JP | 3-229619 A | 10/1991 |
| JP | 4-326940 A | 11/1992 |
| JP | 5-23590 A | 2/1993 |
| JP | 8-192054 A | 7/1996 |
| JP | 11-179207 A | 7/1999 |
| JP | 2012-196654 A | 10/2012 |
| TW | 201217275 A1 | 5/2012 |
| TW | I481556 B | 4/2015 |
| TW | I534082 B | 5/2016 |

OTHER PUBLICATIONS

Morterra et al., 'IR Studies of Carbons-III the Oxidation of Cellulose Chars' in Carbon vol. 22 #1 pp. 5-12 (1984). (Year: 1984).*
Taiwanese Office Action and Search Report, dated Mar. 23, 2018, for Taiwanese Application No. 106120874.
Chinese Office Action and Search Report, dated Feb. 3, 2020, for Chinese Application No. 201710741365.3.
Zhang et al., "Decomposition of Low-Level Ozone in Air over Activated Carbon-Supported Gold Catalyst," Chinese Journal of Catalysis, vol. 29, No. 4, Apr. 2008, pp. 335-340, with an English abstract.

\* cited by examiner

*Primary Examiner* — Stuart L Hendrickson
(74) *Attorney, Agent, or Firm* — Birch, Stewart, Kolasch & Birch, LLP

(57) ABSTRACT

A carbonized material, a device for removing ozone, and a method for removing ozone are provided. The carbonized material has at least a carbonyl-containing group, alkylol group, and carbon having $sp^2$ hybrid orbital. In particular, the at least one carbonyl-containing group has a carbon content from 10 atom % to 30 atom %, based on the total carbon atoms of the at least one carbonyl-containing group, the at least one alkylol group, and the at least one carbon having $sp^2$ hybrid orbital.

10 Claims, 1 Drawing Sheet

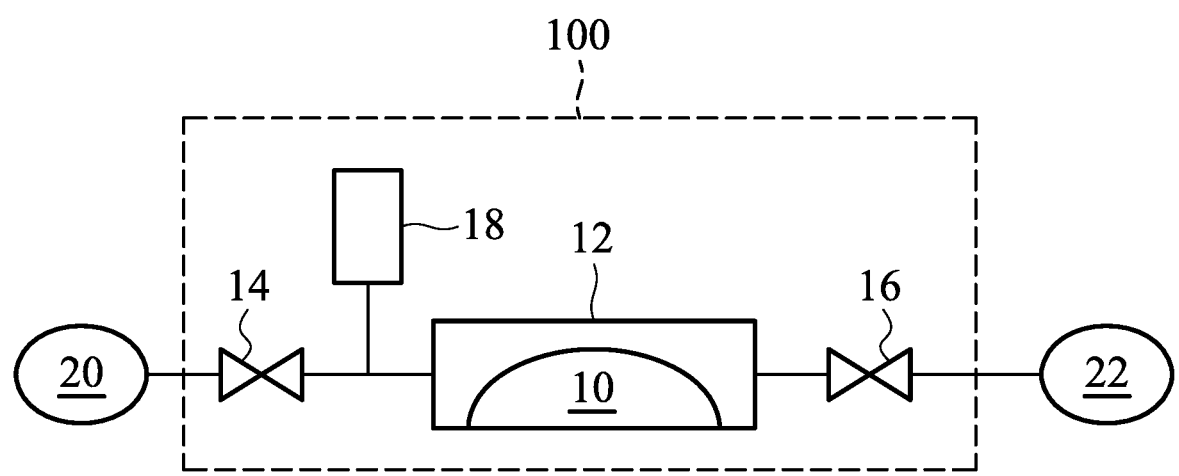

CARBONIZED MATERIAL, DEVICE FOR REMOVING OZONE, AND METHOD FOR REMOVING OZONE

CROSS REFERENCE TO RELATED APPLICATIONS

The application is based on, and claims priority from, Taiwan Application Serial Number 106120874, filed on Jun. 22, 2017, the disclosure of which is hereby incorporated by reference herein in its entirety.

TECHNICAL FIELD

The technical field relates to a carbonized material, a device for removing ozone, and a method for removing ozone.

BACKGROUND

Ozone is widely used for household disinfection, for treating drinking water and sewage, and for the germicidal treatment of facilities and equipment in food processing facilities and similar operations. It is also used for cleaning the surface of wafers in the semiconductor industry. However, the strong oxidative power of ozone can induce health problems such as headache, vomiting, and pulmonary edema, so spent ozone should be decomposed and detoxified after use. Conventional methods for decomposing ozone, however, should be performed under conditions of low humidity or in the presence of an external energy input, which can be the cause of some inconvenience.

Therefore, there is a need to develop a novel material with improved humidity resistance for decomposing ozone in order to reduce the harmful effects of ozone to humans.

SUMMARY

According to embodiments of the disclosure, the disclosure provides a carbonized material. The carbonized material has at least one carbonyl-containing group, at least one alkylol group, and at least one carbon having $sp^2$ hybrid orbital. In particular, the carbonyl-containing group has a carbon content from 10 atom % to 30 atom %, based on the total carbon atoms of the carbonyl-containing group, the alkylol group, and the carbon having $sp^2$ hybrid orbital According to some embodiments of the disclosure, the disclosure also provides a device for removing ozone. The device includes a chamber and the aforementioned carbonized material disposed within the chamber.

According to other embodiments of the disclosure, the disclosure also provides a method for removing ozone. The method includes the following steps. First, a gas is provided, wherein the gas has an ozone concentration that is higher than or equal to about 0.1 ppm. Next, the gas is forced to pass through the carbonized material, such that the ozone of the gas reacts with the carbonized material.

A detailed description is given in the following embodiments with reference to the accompanying drawings.

BRIEF DESCRIPTION OF THE DRAWINGS

FIG. 1 is a schematic view of a device for removing ozone according to embodiments of the disclosure.

DETAILED DESCRIPTION

In the following detailed description, for the purposes of explanation, numerous specific details are set forth in order to provide a thorough understanding of the disclosed embodiments, and wherein the illustrated structures are not necessarily drawn to scale. It will be apparent, however, that one or more embodiments may be practiced without these specific details. In other instances, well-known structures and devices are shown schematically in order to simplify the drawing.

According to embodiments of the disclosure, the disclosure provides a carbonized material, a device for removing ozone, and a method for removing ozone. The carbonized material of the disclosure has specific oxygen-containing group (such as at least one of carbonyl group, carbonyloxy group and oxycarbonyl group). Due to the specific oxygen-containing group having a carbon content within a desired range, the carbonized material of the disclosure can convert the ozone (toxic) into oxygen and carbon dioxide (non-toxic) at room temperature (i.e. in the absence of external energy input). In addition, conventional compounds for decomposing ozone would be inactive in an atmosphere of high humidity. The carbonized material of the disclosure can convert ozone into oxygen and carbon dioxide (non-toxicity) at room temperature (i.e. in the absence of external energy input) in an atmosphere of low or high relative humidity (RH=10%~95%).

Moreover, the carbonized material of the disclosure can be prepared by carbonizing a specific natural material (such as rice husk and waste mushroom bed), thereby increasing the ozone decomposition rate (>99.9%).

According to embodiments of the disclosure, the carbonized material has at least one carbonyl-containing group, and can further include at least one alkylol group and at least one carbon having $sp^2$ hybrid orbital. In particular, the carbonyl-containing group has a carbon content from 10 atom % to 30 atom %, based on the total carbon atoms of the carbonyl-containing group, the alkylol group, and the carbon having $sp^2$ hybrid orbital.

According to embodiments of the disclosure, when the carbonyl-containing group of the carbonized material has a carbon content from 10 atom % to 30 atom % (such as from 10 atom % to 25 atom %), the carbonized material of the disclosure can convert ozone into oxygen and carbon dioxide (non-toxicity) at room temperature (i.e. in the absence of external energy input) in an atmosphere of low or high relative humidity (RH=10%~95%), thereby increasing the ozone decomposition rate (>99.9%).

For example, per gram of the carbonized material can be capable of decomposing 0.8 g-2.0 g of ozone with a relative humidity of 95% at 25° C.

In addition, when the carbonyl-containing group of the carbonized material has a carbon content is too low (i.e. less than 10 atom %), the carbonized material exhibits poor ozone decomposition capability.

According to embodiments of the disclosure, the carbonyl-containing group

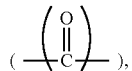

can include at least one of carbonyl group (carbonyl group carbonyloxy

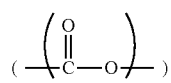

group and oxycarbonyl group

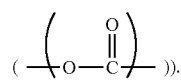

Furthermore, the carbonyl-containing group can be selected from a group consisting of

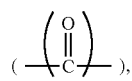

carbonyl group (carbonyl grout carbonyloxy group

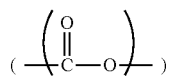

and oxycarbonyl group.

According to embodiments of the disclosure, the carbonized material of the disclosure can be prepared by carbonizing a specific natural material (such as rice husk and waste mushroom bed) via an oxy-fuel combustion process. The disclosure also provides a device for removing ozone. According to embodiments of the disclosure, the device for removing ozone of the disclosure 100 can include the carbonized material of the disclosure 10 and a chamber 12, wherein the carbonized material 10 can be disposed within the chamber 12, as shown in FIG. 1. The chamber 12 carries the carbonized material 10, wherein the chamber 12 is not filled up with the carbonized material 10. According to embodiments of the disclosure, the chamber 12 can be filled up with the carbonized material 10. According to some embodiments of the disclosure, the device for removing ozone 100 can include an inlet 14 and an outlet 16. A raw gas (such as ozone-containing gas) can be introduced into the chamber 12 to react with the carbonized material 10 via the inlet 14. Thus, the ozone of the raw gas 20 can be converted into carbon dioxide and oxygen. The treated gas 22 can be exhausted from the chamber via the outlet 16. The ozone concentration of the raw gas 20 can be greater than or equal to 0.1 ppm, such as from about 0.1 ppm to 5000 ppm, or from about 0.1 ppm to 1%. The ratio of the ozone concentration of the treated gas 22 and the ozone concentration of the raw gas 20 is less than or equal to 0.01, such as from about 0.01 to 0.0001.

According to embodiments of the disclosure, the device for removing ozone of the disclosure 100 can further include a humidifier 18 connected to the chamber 12, as shown in FIG. 1. The humidifier 18 can maintain a specific relative humidity in the chamber. Thus, the ozone of the raw gas 20 can react with the carbonized material 10 under the specific relative humidity (such from about from 10% to 99.9%).

According to embodiments of the disclosure, the device for removing ozone of the disclosure 100 does not include a heating device or a light source. Namely, the carbonized material 10 of the disclosure can convert the ozone into carbon dioxide and oxygen at room temperature. Therefore, in the reaction of the carbonized material of the disclosure and the ozone, heating or irradiating with a light source is no longer necessary.

The disclosure also provides a method for removing ozone. The method includes providing a gas, wherein the gas has an ozone concentration that is higher than or equal to 0.1 ppm. Next, the gas is forced to pass through the carbonized material of the disclosure, such that the ozone of the gas reacts with the carbonized material. According to embodiments of the disclosure, the ozone is converted into carbon dioxide and water after reacting with the carbonized material.

According to embodiments of the disclosure, the ozone of the gas can react with the carbonized material with a relative humidity from 10% to 99%.

Below, exemplary embodiments will be described in detail with reference to the accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

EXAMPLES

Preparation of Carbonized Material

Example 1

5 kg of dried rice husk was introduced into a carbonization furnace via a feed inlet. After feeding, a mixture of oxygen gas and air (the mixture had an oxygen concentration that was greater than 20%) was introduced into the carbonization furnace at a flow rate of 60 L/min. Next, after combustion at 800° C. for 50 min, pure water was introduced into the carbonization furnace at a flow rate of 3 L/min for about 5 min. Next, the result was dried at 50° C. for 24 hr, obtaining Carbonized material (1).

The carbon content of the oxygen-containing groups (including carbonyloxy group, oxycarbonyl group, carbonyl group and alkylol group) and the carbon having an $sp^2$ hybrid orbital of Carbonized material (1) was determined by X-ray photoelectron spectroscopy (XPS), and the results are shown in Table 1.

Example 2

10 kg of dried waste mushroom bed was introduced into a carbonization furnace via a feed inlet. After feeding, a mixture of oxygen gas and air (the mixture had an oxygen concentration that was greater than 20%) was introduced into the carbonization furnace at a flow rate of 60 L/min. Next, after combustion at 800° C. for 50 min, pure water was introduced into the carbonization furnace at a flow rate of 3 L/min for about 5 min. Next, the result was dried at 50° C. for 24 hr, obtaining Carbonized material (2).

The carbon content of the oxygen-containing groups (including carbonyloxy group, oxycarbonyl group, carbonyl group and alkylol group) and the carbon having an $sp^2$ hybrid orbital of Carbonized material (2) was determined by X-ray photoelectron spectroscopy (XPS), and the results are shown in Table 1.

Comparative Example 1

500 g of dried wood sawdust was introduced into a carbonization furnace via a feed inlet. The carbonization furnace was heated at a heating rate of 15° C./hr. After combustion at 800° C. for 60 min in the absence of introduced gas, pure water was introduced into the carbonization furnace at a flow rate of 3 L/min for about 5 min. Next, the result was dried at 50° C. for 24 hr, obtaining Carbonized material (3).

The carbon content of the oxygen-containing groups (including carbonyloxy group, oxycarbonyl group, carbonyl group and alkylol group) and the carbon having an $sp^2$ hybrid orbital of Carbonized material (3) was determined by X-ray photoelectron spectroscopy (XPS), and the results are shown in Table 1.

TABLE 1

| | Carbon content (atom %) (based on the total carbon atoms of carbonyloxy groups, oxycarbonyl groups, carbonyl groups, alkylol groups, and carbons having $sp^2$ hybrid orbital of the carbonized material) | | | |
|---|---|---|---|---|
| | carbonyloxy group and oxycarbonyl group | carbonyl group | alkylol group | carbon having $sp^2$ hybrid orbital |
| Carbonized material (1) | 9.4 | 15.4 | 25.0 | 50.2 |
| Carbonized material (2) | ~0 | 10.6 | 10.1 | 79.3 |
| Carbonized material (3) | ~0 | 4.6 | 32.3 | 63.1 |

As shown in Table 1, the carbon content of all the carbonyl-containing groups (including carbonyloxy groups, oxycarbonyl groups and carbonyl groups) of Carbonized material (1) is about 24.8 atom %, and the carbon content of all the carbonyl-containing groups of Carbonized material (2) is about 10.6 atom %, and the carbon content of all the carbonyl-containing groups of Carbonized material (3) is about 4.6 atom %.

Example 3

10.7 g of Carbonized material (1) of Example 1 was introduced into a reaction chamber, and the temperature of the reaction chamber was maintained at 25° C. Next, a gas (having an ozone concentration of about 292.9 ppm) was introduced into the reaction chamber via a mass flow controller (MFC), wherein the flow rate of the gas was L/min and the flow velocity was 0.09 m/s. A humidifier adjusted the relative humidity of the reaction chamber to greater than about 95%. The ozone concentration of the treated gas passing through the outlet was determined by an ozone detector (having a lower detection limit of about 0.01 ppm). During the introduction of the gas having an ozone concentration of about 292.9 ppm, the ozone detector revealed that the treated gas had no ozone concentration. Accordingly, the ozone decomposition rate of the device employing Carbonized material (1) was about 99.9%. The ozone detector revealed that the treated gas had an ozone concentration that was greater than or equal to about 1 ppm, when the introduction of the gas took 99.3 hr. The ozone decomposition amount per gram of Carbonized material (1) was determined by means of the weight of Carbonized material (1), ozone concentration and process time, and the result is shown in Table 2.

Example 4

18.6 g of Carbonized material (1) of Example 2 was introduced into a reaction chamber, and the temperature of the reaction chamber was maintained at 25° C. Next, a gas (having an ozone concentration of about 313.9 ppm) was introduced into the reaction chamber via a mass flow controller (MFC), wherein the flow rate of the gas was L/min and the flow velocity was 0.09 m/s. A humidifier adjusted the relative humidity of the reaction chamber to greater than about 95%. The ozone concentration of the treated gas passing through the outlet was determined by an ozone detector (having a lower detection limit of about 0.01 ppm). During the introduction of the gas having an ozone concentration of about 313.9 ppm, the ozone detector revealed that the treated gas had no ozone concentration. Accordingly, the ozone decomposition rate of the device employing Carbonized material (2) was about 99.9%. The ozone detector revealed that the treated gas had an ozone concentration that was greater than or equal to about 1 ppm, when the introduction of the gas took 99.3 hr. The ozone decomposition amount per gram of Carbonized material (2) was determined by means of the weight of Carbonized material (2), ozone concentration and process time, and the result is shown in Table 2.

Comparative Example 2

28.6 g of Carbonized material (3) of Comparative Example 1 was introduced into a reaction chamber, and the temperature of the reaction chamber was maintained at 25° C. Next, a gas (having an ozone concentration of about 364 ppm) was introduced into the reaction chamber via a mass flow controller (MFC), wherein the flow rate of the gas was L/min and the flow velocity was 0.09 m/s. A humidifier adjusted the relative humidity of the reaction chamber to greater than about 95%. The ozone concentration of the treated gas passing through the outlet was determined by an ozone detector (having a lower detection limit of about 0.01 ppm). During the introduction of the gas having an ozone concentration of about 364 ppm, the ozone detector revealed that the treated gas had no ozone concentration. Accordingly, the ozone decomposition rate of the device employing Carbonized material (3) was about 99.9%. The ozone detector revealed that the treated gas had an ozone concentration that was greater than or equal to about 1 ppm, when the introduction of the gas took 25 min. The ozone decomposition amount per gram of Carbonized material (3) was determined by means of the weight of Carbonized material (3), ozone concentration and process time, and the result is shown in Table 2.

TABLE 2

| | Carbon content of all carbonyl-containing groups of the carbonized material (atom %) | carbonyl-containing group (g/g) |
|---|---|---|
| Example 3 | 24.8 | 1.60 |
| Example 4 | 10.6 | 0.98 |
| Comparative Example 2 | 4.6 | 0.003 |

As shown in Table 2, since the carbonized material of the disclosure have specific carbonyl-containing group (such as at least one of carbonyl group, carbonyloxy group and oxycarbonyl group) and the carbon content of all carbonyl-containing groups of the carbonized material of the disclosure is within a range from 10 atom % to 30 atom %, the carbonized material of the disclosure can decompose ozone under high relative humidity at room temperature. Furthermore, the carbonized materials of the disclosure exhibit high ozone decomposition capability. For example, 1.0 g of the carbonized material of the disclosure is capable of decomposing 0.8 g-2.0 g of ozone with a relative humidity greater than or equal to 95% at 25° C.

Example 5

27.7 g of Carbonized material (1) of Example 1 was introduced into a reaction chamber, and the temperature of the reaction chamber was maintained at 25° C. Next, a gas (having an ozone concentration of about 154.9 ppm) was introduced into the reaction chamber via a mass flow controller (MFC), wherein the flow rate of the gas was L/min and the flow velocity was 0.09 m/s. A humidifier adjusted the relative humidity of the reaction chamber to about 42%. The ozone concentration of the treated gas passing through the outlet was determined by an ozone detector (having a lower detection limit of about 0.01 ppm). During the introduction of the gas having an ozone concentration of about 154.9 ppm, the ozone detector revealed that the treated gas had no ozone concentration. Accordingly, the ozone decomposition rate of the device employing Carbonized material (1) was about 99.9%. The ozone detector revealed that the treated gas had an ozone concentration that was greater than or equal to about 1 ppm, when the introduction of the gas took 176.5 hr. The ozone decomposition amount per gram of Carbonized material (1) was determined by means of the weight of Carbonized material (1), ozone concentration and process time, and the result is shown in Table 3.

Example 6

28.4 g of Carbonized material (1) of Example 1 was introduced into a reaction chamber, and the temperature of the reaction chamber was maintained at 25° C. Next, a gas (having an ozone concentration of about 365.9 ppm) was introduced into the reaction chamber via a mass flow controller (MFC), wherein the flow rate of the gas was L/min and the flow velocity was 0.09 m/s. A humidifier adjusted the relative humidity of the reaction chamber to about 12%. The ozone concentration of the treated gas passing through the outlet was determined by an ozone detector (having a lower detection limit of about 0.01 ppm). During the introduction of the gas having an ozone concentration of about 365.9 ppm, the ozone detector revealed that the treated gas had no ozone concentration. Accordingly, the ozone decomposition rate of the device employing Carbonized material (1) was about 99.9%. The ozone detector revealed that the treated gas had an ozone concentration that was greater than or equal to about 1 ppm, when the introduction of the gas took 10.8 hr. The ozone decomposition amount per gram of Carbonized material (1) was determined by means of the weight of Carbonized material (1), ozone concentration and process time, and the result is shown in Table 3.

TABLE 3

|  | relative humidity | ozone decomposed amount (g/g) |
| --- | --- | --- |
| Example 3 | ≥95% | 1.60 |
| Example 5 | 42% | 0.58 |
| Example 6 | 12% | 0.08 |

As shown in Table 3, the ozone decomposition capability of the carbonized material of the disclosure is directly proportional to the relative humidity. Unlike conventional carbonized material, the carbonized material of the disclosure would not be inactive in an atmosphere of high humidity. Therefore, the carbonized material of the disclosure is suitable for treatment with ozone under high relative humidity. In addition, the carbonized material of the disclosure exhibits ozone decomposition capability under low relative humidity.

It will be clear that various modifications and variations can be made to the disclosed methods and materials. It is intended that the specification and examples be considered as exemplary only, with the true scope of the disclosure being indicated by the following claims and their equivalents.

What is claimed is:

1. A carbonized material, comprising: at least one carbonyl-containing group; at least one alkylol group; and at least one carbon having $sp^2$ hybrid orbital, wherein the at least one carbonyl-containing group has a carbon content from 10 atom % to 30 atom %, based on the total carbon atoms of the at least one carbonyl-containing group, the at least one alkylol group, and the at least one carbon having $sp^2$ hybrid orbital.

2. The carbonized material as claimed in claim 1, wherein the carbonyl-containing group is selected from the group consisting of carbonyl group, carbonyloxy group and oxycarbonyl group.

3. The carbonized material as claimed in claim 1, wherein the at least one carbonyl-containing group has a carbon content from 10 atom % to 25 atom %, based on the total carbon atoms of the at least one carbonyl-containing group, the at least one alkylol group, and the at least one carbon having $sp^2$ hybrid orbital.

4. The carbonized material as claimed in claim 1, wherein 1.0 g of the carbonized material is capable of decomposing 0.8 g-2.0 g of ozone with a relative humidity of 95% at 25° C.

5. A device for removing ozone, comprising:
a chamber; and
the carbonized material as claimed in claim 1, disposed within the chamber.

6. The device for removing ozone as claimed in claim 5, further comprising:
an inlet for introducing a gas into the chamber; and
an outlet for exhausting the gas passing through the carbonized material from the chamber.

7. The device for removing ozone as claimed in claim 6, further comprising:
a humidifier connected to the chamber in order to maintain a specific relative humidity in the chamber.

8. A method for removing ozone, comprising:
providing a gas, wherein the gas has an ozone concentration that is higher than or equal to 0.1 ppm; and
forcing the gas to pass through the carbonized material as claimed in claim 1, such that the ozone of the gas reacts with the carbonized material.

9. The method as claimed in claim 8, wherein the ozone is converted into carbon dioxide and water after reacting with the carbonized material.

10. The method as claimed in claim 8, wherein the ozone of the gas reacts with the carbonized material with a relative humidity from 10% to 99%.

* * * * *